(12) United States Patent
Lee et al.

(10) Patent No.: US 10,064,908 B2
(45) Date of Patent: Sep. 4, 2018

(54) METHOD FOR PREVENTING, IMPROVING OR TREATING LIVER DISEASE

(71) Applicant: Wonkwang University Center for Industry-Academy Cooperation, Jeollabuk-do (KR)

(72) Inventors: Young Mi Lee, Jeollabuk-do (KR); Dae Ki Kim, Jeollabuk-do (KR); Hyeon Hui Ki, Jeollabuk-do (KR); Hoon Yeon Lee, Jeollabuk-do (KR)

(73) Assignee: Wonkwang University Center for Industry-Academy Cooperation, Jeollabuk-do (KR)

( * ) Notice: Subject to any disclaimer, the term of this patent is extended or adjusted under 35 U.S.C. 154(b) by 0 days.

(21) Appl. No.: 15/448,031

(22) Filed: Mar. 2, 2017

(65) Prior Publication Data

US 2017/0252395 A1    Sep. 7, 2017

(30) Foreign Application Priority Data

Mar. 3, 2016 (KR) .................. 10-2016-0025565

(51) Int. Cl.
*A61K 36/899* (2006.01)

(52) U.S. Cl.
CPC ...... *A61K 36/899* (2013.01); *A61K 2236/333* (2013.01)

(58) Field of Classification Search
None
See application file for complete search history.

(56) References Cited

U.S. PATENT DOCUMENTS

2014/0295011 A1* 10/2014 Lee .................. A61K 36/899
424/774

FOREIGN PATENT DOCUMENTS

KR    101160575 B1    6/2012

OTHER PUBLICATIONS

Tirger et al. Investigation Into Beeficial Effects of Triticum Aestivum (Wheat Grass) Iron Overload Complications. Pharmacologyonline 2: 900-920. (Year: 2011).*
Kerton, F.M. Chapter 5.2 Chemical Examples: 5.2.1 Alcohols including Glycerol from "Alternative Solvents for Green Chemistry". Royal Society of Chemistry, pp. 1102.. (Year: 2009).*
Roh et al "Massa Medicata Fermentata Improves Fatty Liver in High Fat Diet—Fed Nonalcoholic Fatty Liver Disease's Mouse Model" Korean Journal of Herbology vol. 29, pp. 23-31, 2014.

* cited by examiner

*Primary Examiner* — Amy Lynn Clark
(74) *Attorney, Agent, or Firm* — Cesari and McKenna, LLP

(57) ABSTRACT

The present invention provides a method for preventing, alleviating or treating a liver disease, comprising administering a composition comprising a *Triticum aestivum* Lamarck leaf extract or a fraction thereof to a subject in need thereof. Therefore, the method for preventing, alleviating or treating a liver disease of the present invention can improve the morphological change of liver tissue due to liver injury, inhibit apoptosis of hepatocytes, increase the synthesis of antioxidant enzymes such as glutathione (GSH) and superoxide dismutase (SOD) which can reduce oxidative stress in liver tissue, and reduce the levels of glutamic oxaloacetic transaminase (GOT) and glutamic pyruvic transaminase (GPT) which are known to change sensitively in liver diseases.

6 Claims, 16 Drawing Sheets

[Fig 1]
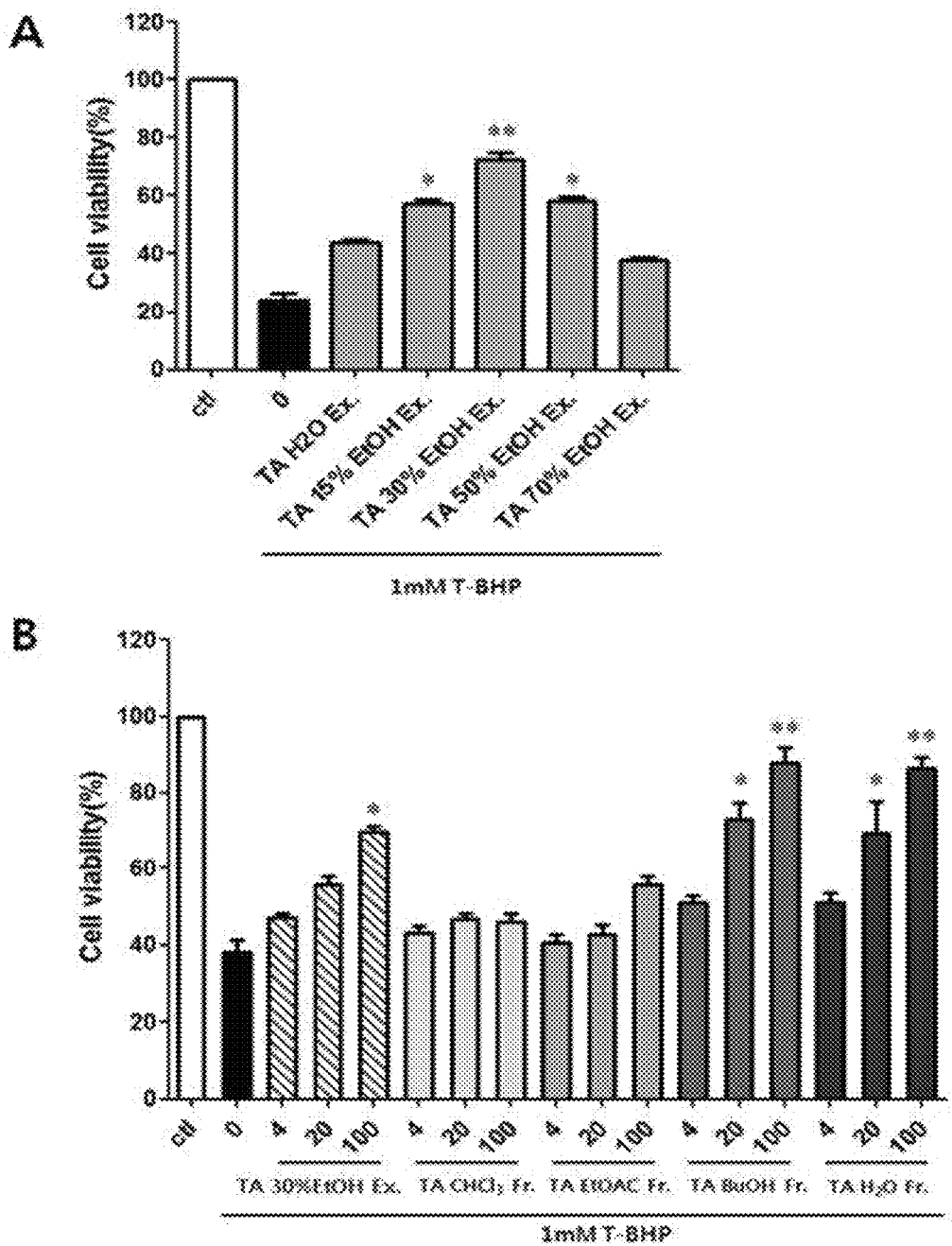

[Fig 2]
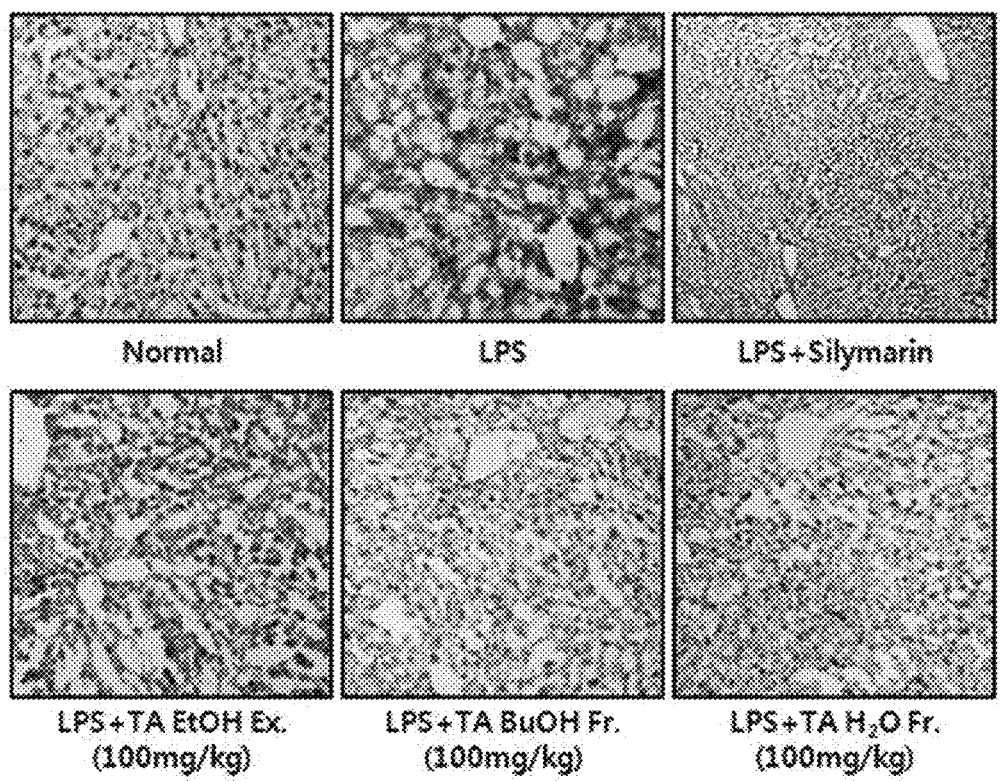

[Fig 3]
A
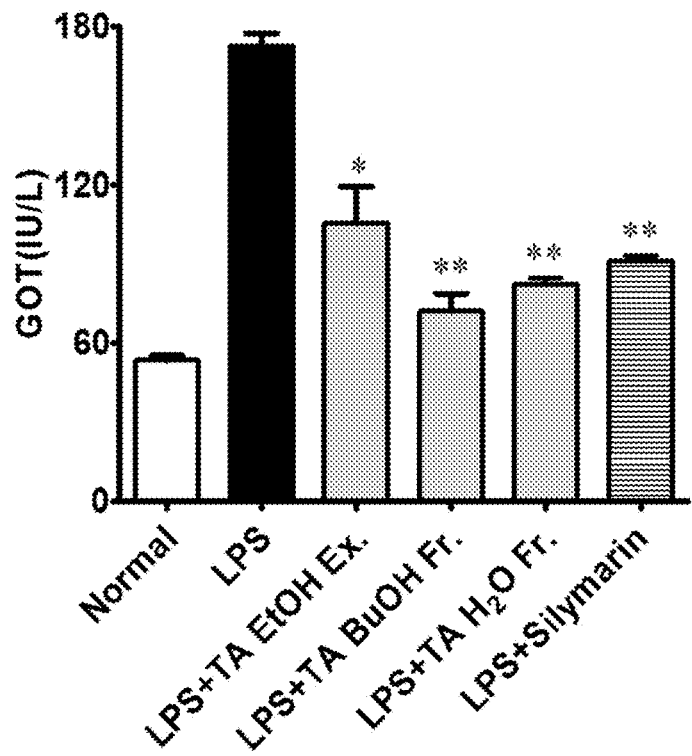
B
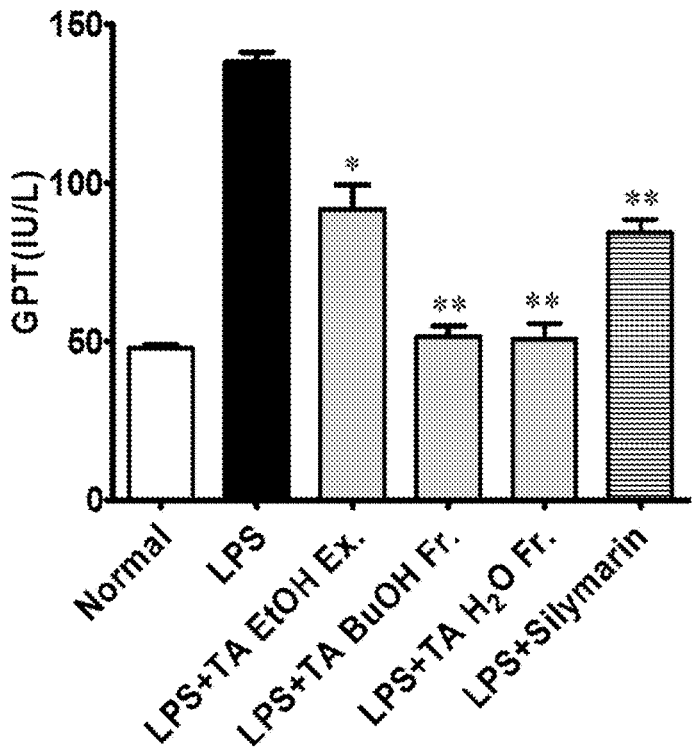

[Fig 4]
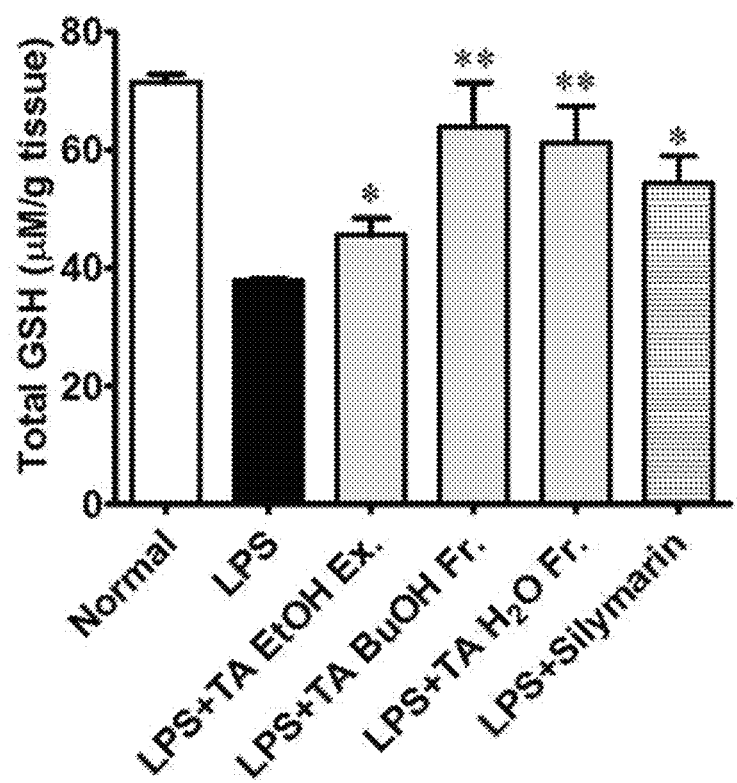

[Fig 5]
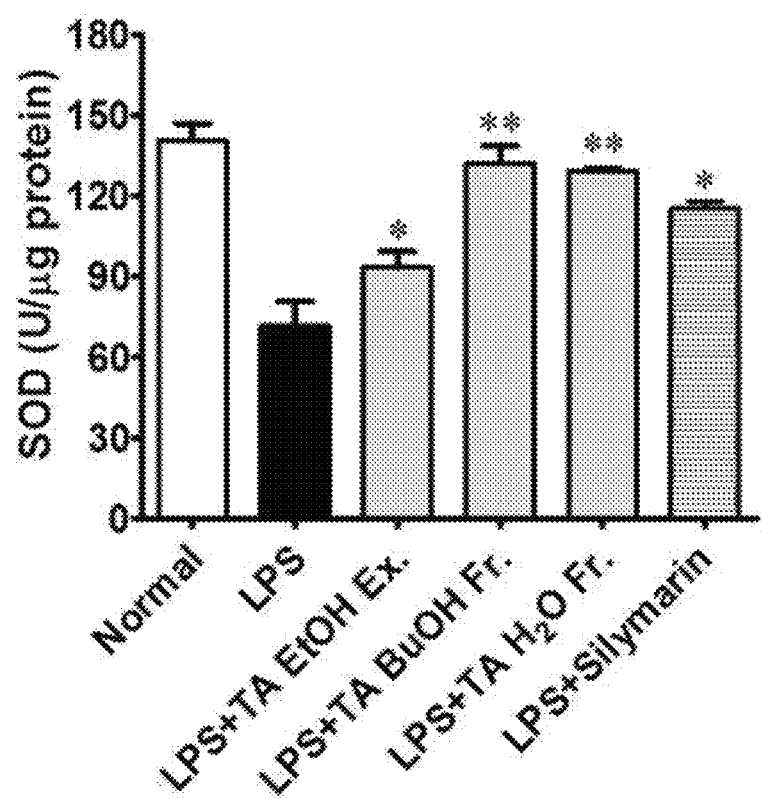

[Fig 6]
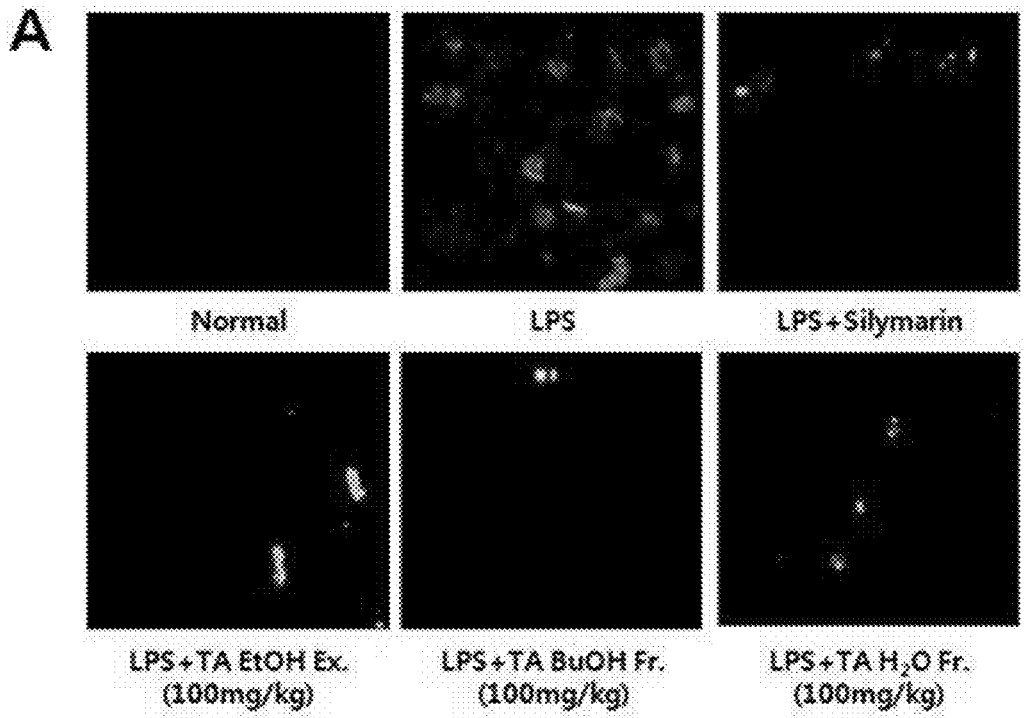
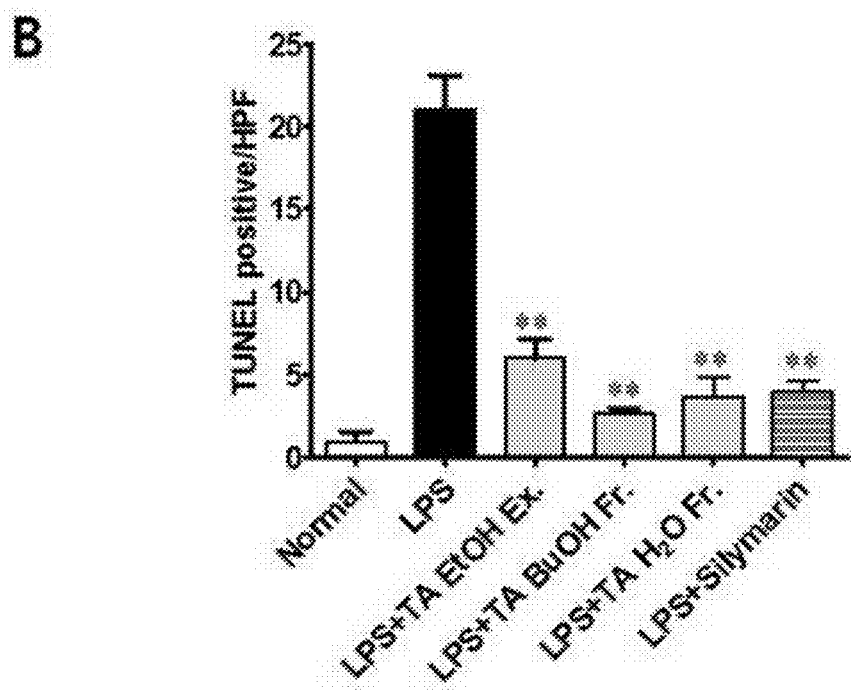

[Fig 7]
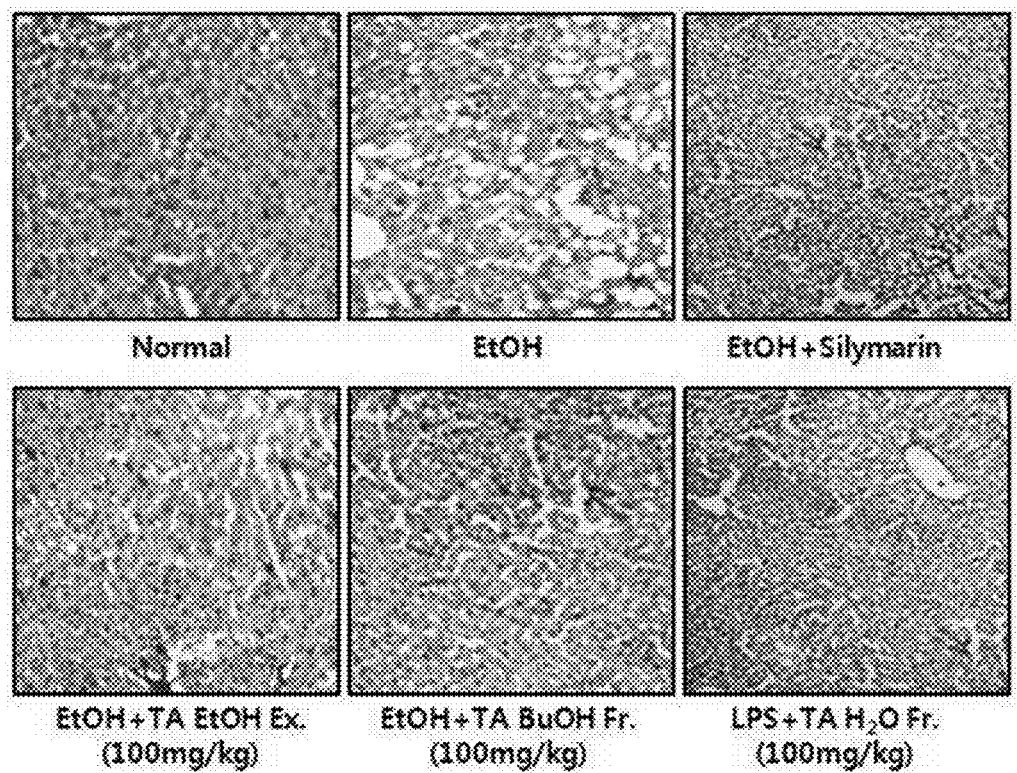

[Fig 8]
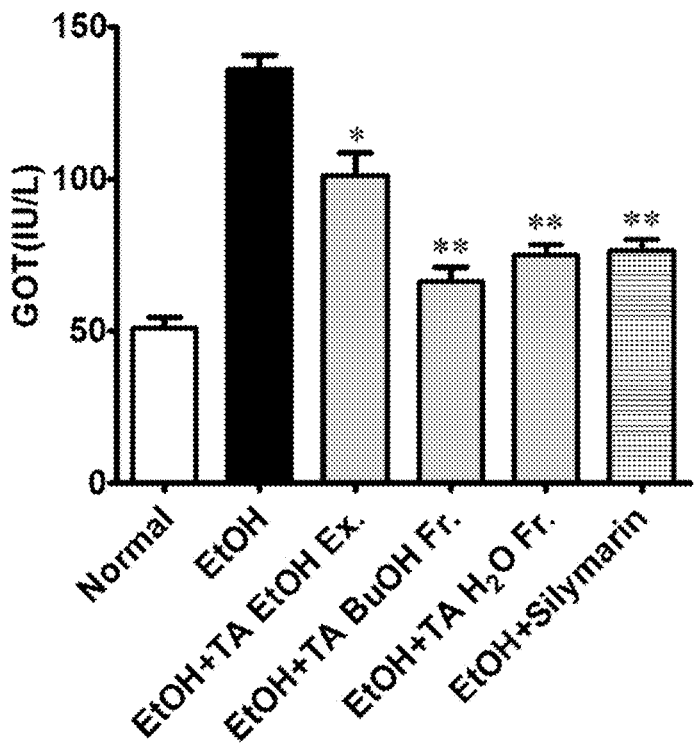
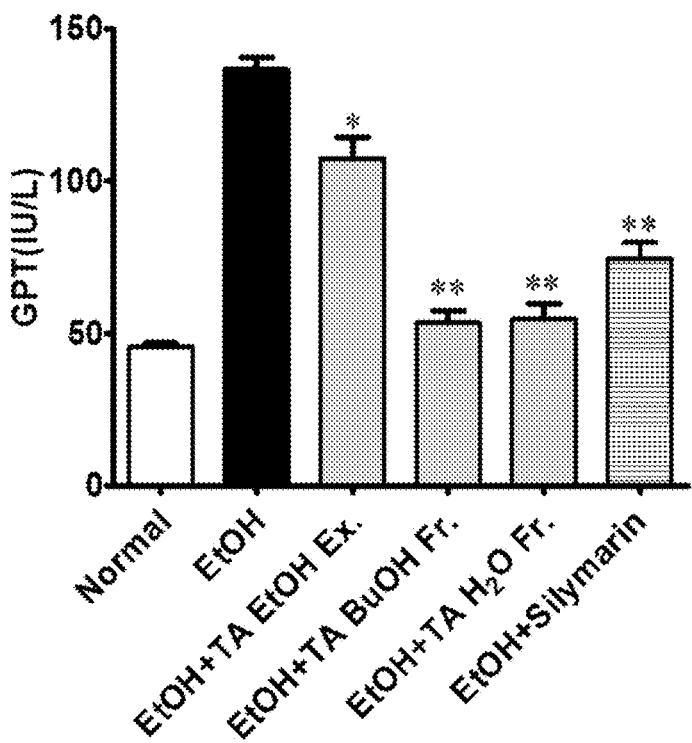

[Fig 9]
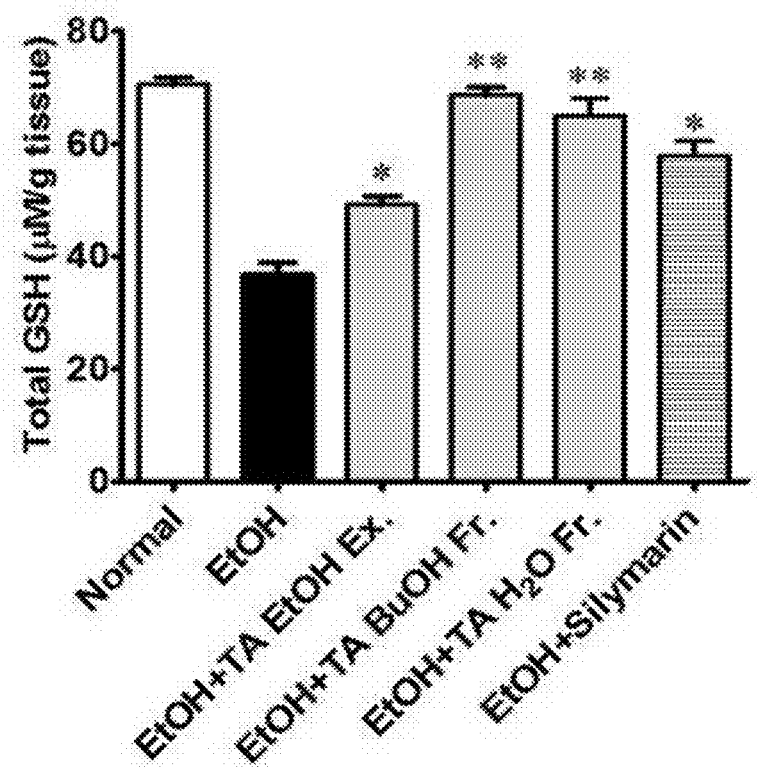

[Fig 10]
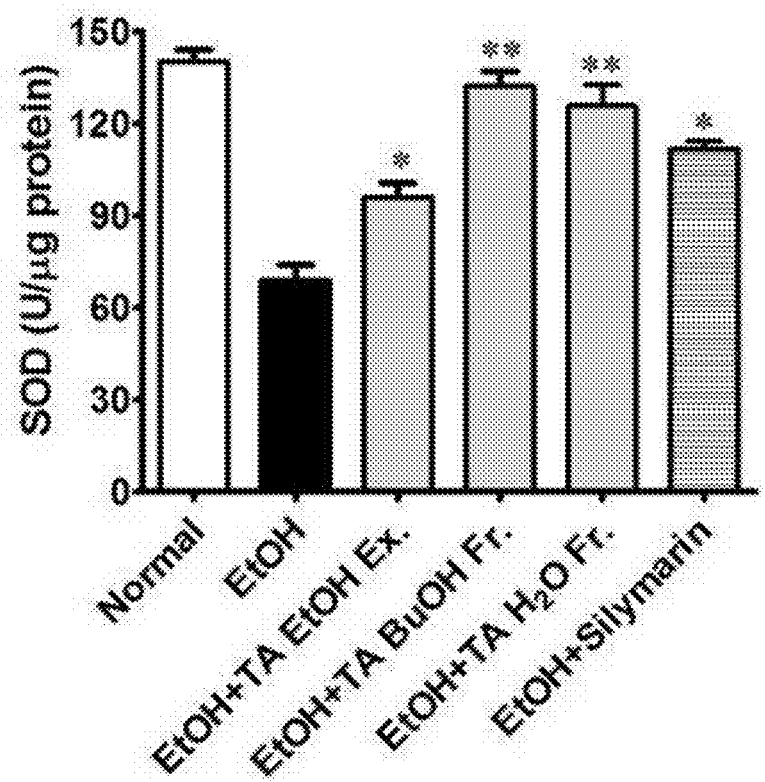

[Fig 11]
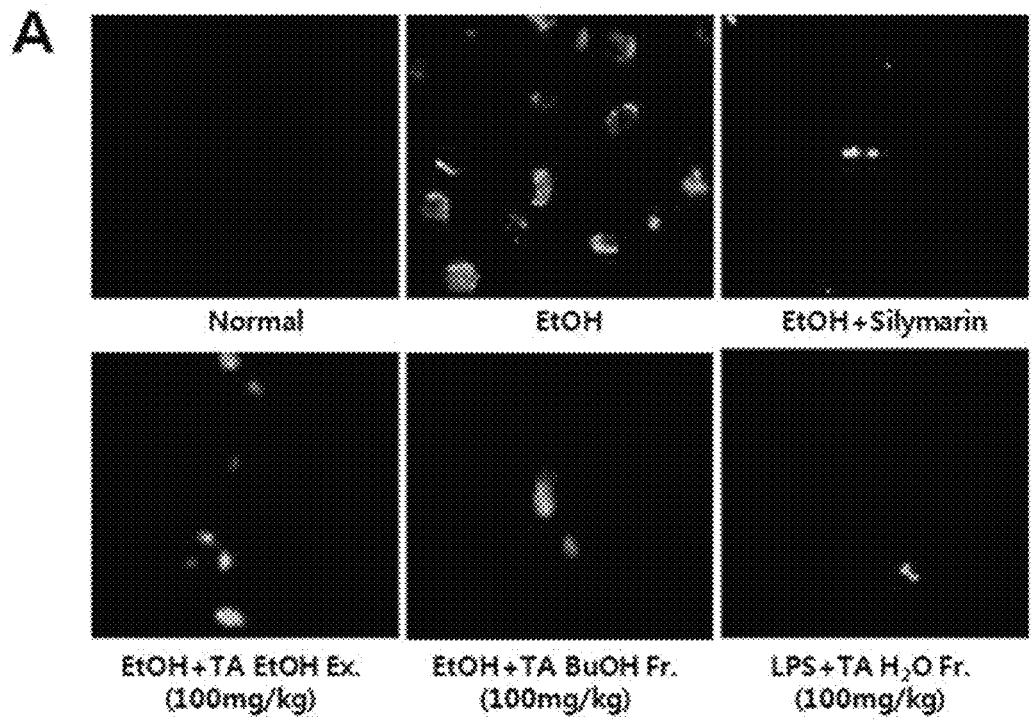
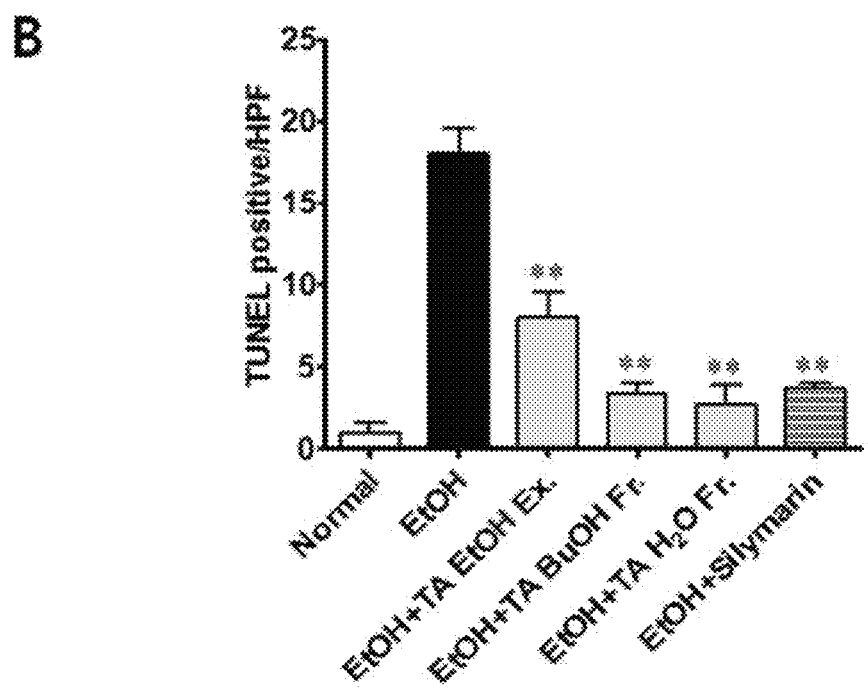

[Fig 12]
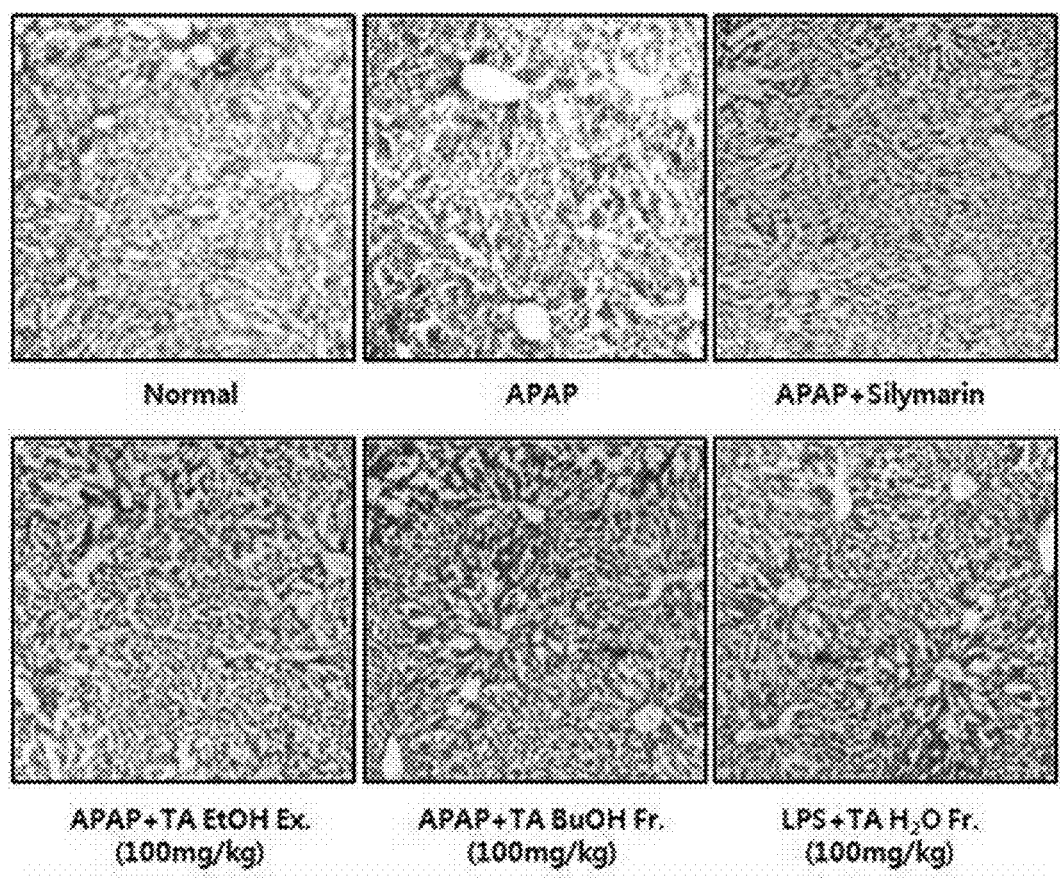

[Fig 13]
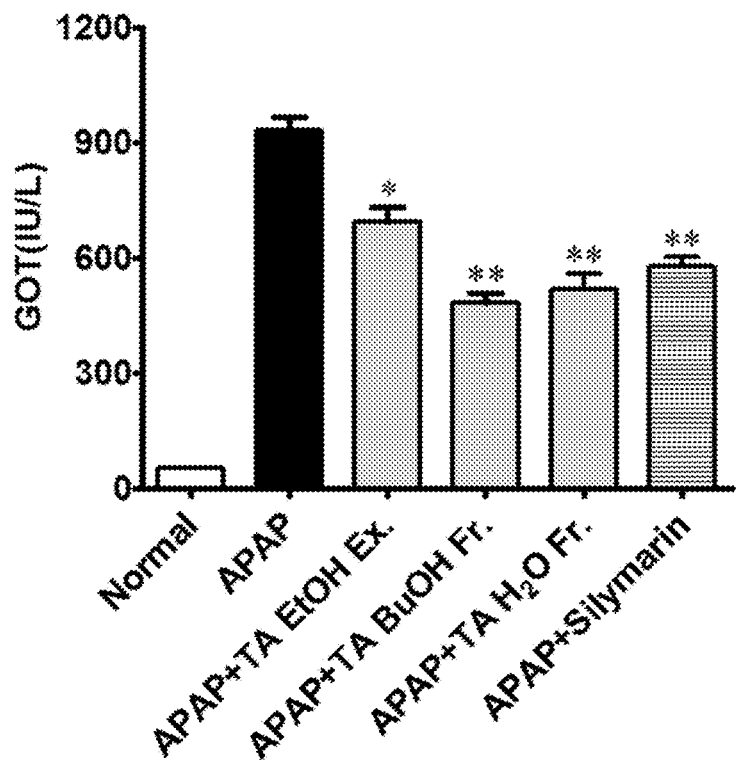
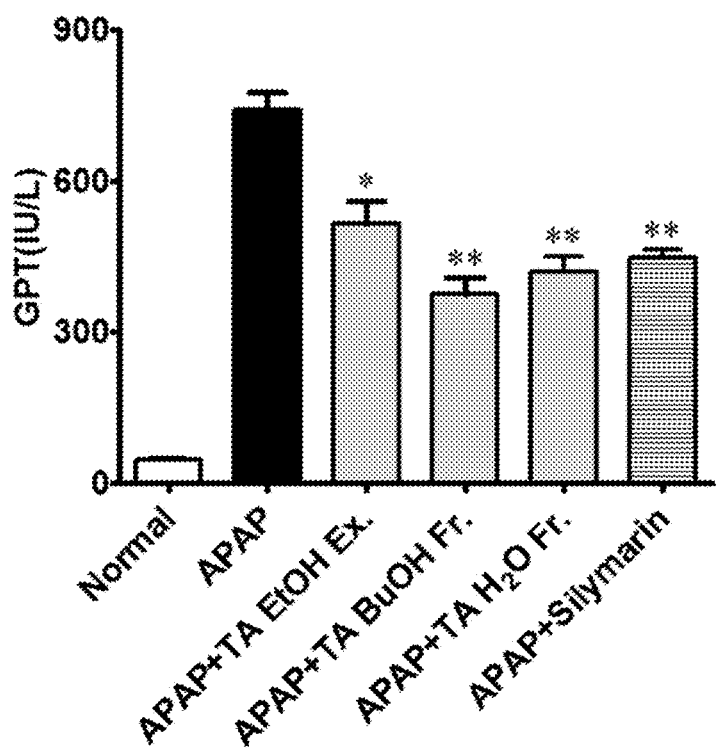

[Fig 14]
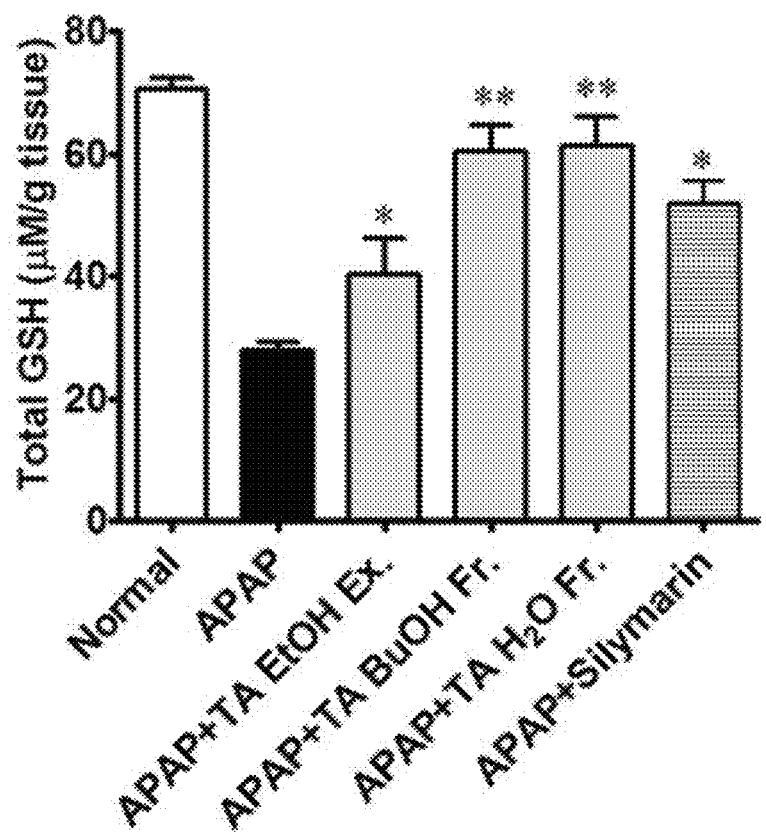

[Fig 15]
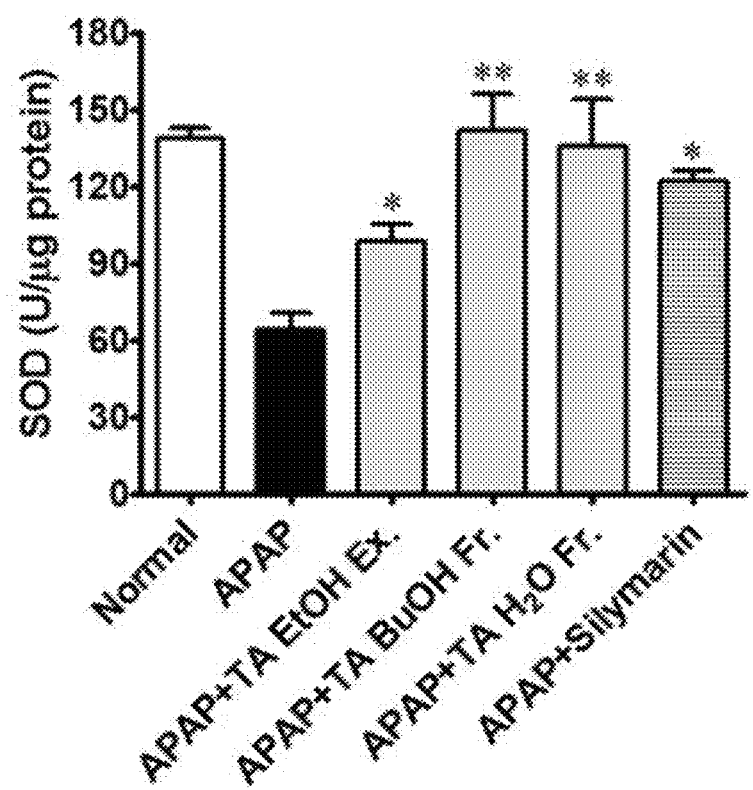

[Fig 16]
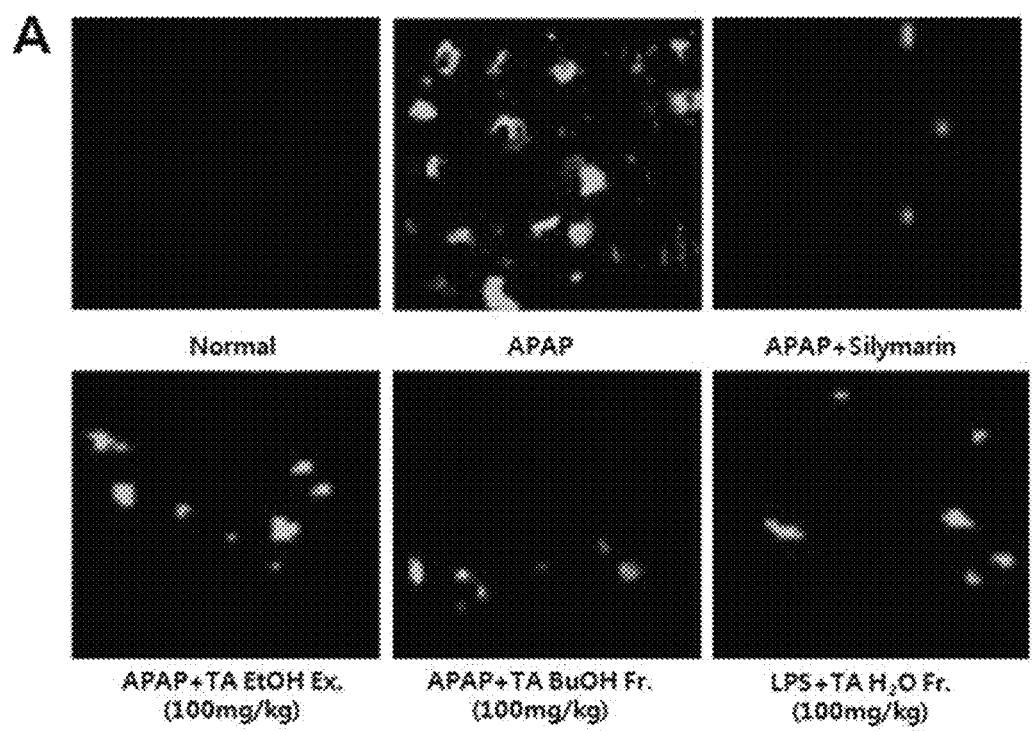
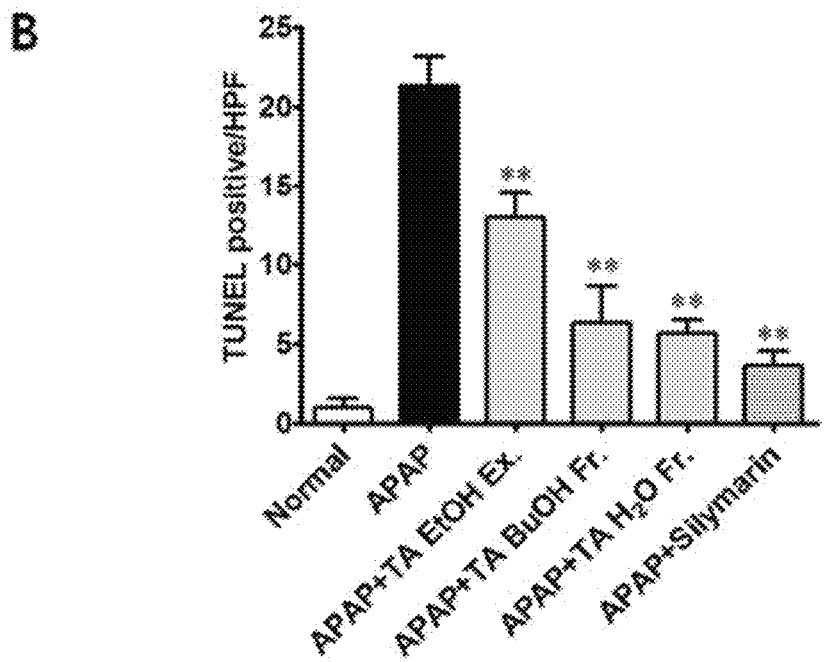

METHOD FOR PREVENTING, IMPROVING OR TREATING LIVER DISEASE

CROSS-REFERENCE TO RELATED PATENT APPLICATION

This application claims the benefit of Korean Patent Application No. 10-2016-0025565, filed on Mar. 3, 2016, the disclosure of which is incorporated herein in its entirety by reference.

BACKGROUND OF THE INVENTION

1. Field of the Invention

The present invention relates to a method for preventing, alleviating or treating a liver disease and, more specifically, to a method for preventing, alleviating or treating a liver disease, comprising administering a composition comprising a *Triticum aestivum* Lamarck leaf extract or a fraction thereof to a subject in need thereof.

2. Description of the Related Art

The liver is an important organ that is responsible for metabolism of various nutrients and hormones introduced into the body as well as for detoxification of harmful substances. Due to the buffering effect of the liver, minor damage to the liver by hepatotoxic factors can be recovered and does not develop into liver disease. However, persistent liver injury due to continuous exposure to excessive intake of drugs or alcohol, stress, etc. may lead to inflammation of the liver and is highly likely to develop into a series of chronic liver diseases such as chronic hepatitis, cirrhosis, and liver cancer.

It is known that liver injury is mainly caused by depletion of antioxidant enzymes due to oxidative stress and by dysfunction of hepatocytes that can prevent liver injury. Moreover, apoptosis of hepatocytes is involved in almost all types of human liver injuries and is an important parameter for the detection of acute and chronic liver diseases including liver injury induced by viral and bacterial infections, exposure to toxic substances, metabolic dysfunction, autoimmune reaction, etc. Many clinical studies and animal models have reported that apoptosis of hepatocytes is an important factor in the development of liver diseases including inflammation, hepatic fibrosis, cirrhosis, and liver cancer.

Examples of substances that cause liver injury include lipopolysaccharide (LPS), alcohol, acetaminophen, carbon tetrachloride ($CCl_4$), D-galactosamine, bromobenzene, etc.

The liver is the organ that mainly acts on the removal of endotoxins that enter the body, and thus the penetration of endotoxins into the body causes liver injury. Among others, lipopolysaccharide (LPS) is one of the substances, which constitute the cell wall of Gram-negative bacteria, and interacts with toll-like receptor 4 present in Kupffer cells and other cells to increase the production of proinflammatory cytokines such as tumor necrosis factors (TNF-$\alpha$), interleukin 1 (IL-6), and interleukin 6 (IL-6), thereby causing oxidative stress and inflammatory responses, leading to liver injury.

Moreover, the liver is the major organ of alcohol metabolism, and after intake, alcohol is converted to acetaldehyde by alcohol dehydrogenase, CYP2E1 and catalase. Excessive intake of alcohol causes excessive acetaldehyde production, which inhibits the production of antioxidants such as glutathione (GSH) that reduces oxidative stress, leading to liver injury, which increases the risk of alcoholic liver diseases such as cirrhosis, and liver fibrosis.

In addition, excessive intake of acetaminophen, a drug component that inhibits the biosynthesis of prostaglandin in the body to exhibit an analgesic effect, causes liver injury. When absorbed into the body, acetaminophen is detoxified with a combination of gluconic acid and sulfate, and a portion thereof is converted to N-acetyl-p-benzoquinoneimine to exhibit hepatotoxicity, which is neutralized by antioxidant enzymes such as glutathione. However, excessive administration of acetaminophen produces a large amount of N-acetyl-p-benzoquinoneimine, which causes depletion of glutathione in hepatocytes and apoptosis of hepatocytes due to cytotoxicity, leading to liver injury.

Chronic liver injury is often not recognized until the liver loses its functions of detoxification and protection and is a major cause of liver diseases. Interferon, ursodeoxycholic acid, silymarin, vitamin B, etc. have been used for the treatment of hepatitis and cirrhosis and for the improvement of liver function, but there is a lack of naturally occurring materials which can be safely ingested and activated to improve liver injury.

Meanwhile, *Triticum aestivum* Lamarck is one of the main crops produced worldwide and produces useful components during germination, and *Triticum aestivum* Lamarck leaves refer to those sprouting from *Triticum aestivum* Lamarck.

SUMMARY OF THE INVENTION

In the present invention, as a result of confirming the effect of *Triticum aestivum* Lamarck leaves on the improvement of liver injury, it has been confirmed that *Triticum aestivum* Lamarck leaf extracts and fractions thereof improve liver tissue injury due to toxicity of Lipopolysaccharide (LPS), alcohol and acetaminophen in animal models, and the present invention has been completed.

Accordingly, an object of the present invention is to provide a method for preventing, alleviating or treating a liver disease, comprising administering a composition comprising a *Triticum aestivum* Lamarck leaf extract or a fraction thereof to a subject in need thereof, thereby alleviating the morphological change of liver tissue due to liver injury, inhibiting apoptosis of hepatocytes, increasing the synthesis of antioxidant enzymes such as glutathione (GSH) and superoxide dismutase (SOD) which can reduce oxidative stress in liver tissue, and reducing the levels of glutamic oxaloacetic transaminase (GOT) and glutamic pyruvic transaminase (GPT) which are known to change sensitively in liver diseases.

In order to achieve the above object, the present invention provides a method for preventing, alleviating or treating a liver disease, comprising administering a composition comprising a *Triticum aestivum* Lamarck leaf extract or a fraction thereof to a subject in need thereof.

The *Triticum aestivum* Lamarck leaf extract may preferably be an extract obtained by extraction with at least one solvent selected from the group consisting of water, an alcohol having 1 to 4 carbon atoms, and a mixture thereof.

In particular, the present invention provides a method for preventing, alleviating or treating a liver disease, wherein the *Triticum aestivum* Lamarck leaf extract is a 15-50% (v/v) ethanol extract.

The *Triticum aestivum* Lamarck leaf fraction may preferably be a fraction obtained by fractionation with at least one solvent selected from the group consisting of chloroform, ethyl acetate, butanol, and water.

Moreover, the present invention provides a method of preventing or alleviating liver injury or dysfunction, comprising administering a composition comprising a *Triticum aestivum* Lamarck leaf extract or a fraction thereof to a subject in need thereof.

BRIEF DESCRIPTION OF THE DRAWINGS

The above and other features and advantages of the present invention will become more apparent by describing in detail exemplary embodiments thereof with reference to the attached drawings in which:

FIG. 1 shows the effects on cell viability in HepG2 cell lines with cell damage induced by tertiary butyl hydroperoxide, after treatment with *Triticum aestivum* Lamarck leaf extracts and fractions thereof in accordance with an embodiment of the present invention, where A is a graph showing the results of treatment with a water extract of *Triticum aestivum* Lamarck leaves and ethanol extracts at various concentrations and B is a graph showing the results of treatment with a fraction obtained by fractionation of a 30% ethanol extract.

FIG. 2 shows the effects of administration of *Triticum aestivum* Lamarck leaf extracts and fractions thereof on liver tissue of mice with liver injury induced by LPS in accordance with an embodiment of the present invention.

FIG. 3 shows the effects of *Triticum aestivum* Lamarck leaf extracts and fractions thereof on GOT and GPT levels in serum of mice with liver injury induced by LPS in accordance with an embodiment of the present invention, where A is a graph showing the results of GOT and B is a graph showing the results of GPT.

FIG. 4 is a graph showing the effects of *Triticum aestivum* Lamarck leaf extracts and fractions thereof on GSH level in liver tissue of mice with liver injury induced by LPS in accordance with an embodiment of the present invention.

FIG. 5 is a graph showing the effects of *Triticum aestivum* Lamarck leaf extracts and fractions thereof on SOD level in liver tissue of mice with liver injury induced by LPS in accordance with an embodiment of the present invention.

FIG. 6 shows the effects of *Triticum aestivum* Lamarck leaf extracts and fractions thereof on the inhibition of apoptosis of hepatocytes in mice with liver injury induced by LPS in accordance with an embodiment of the present invention, where A shows images of TUNEL-positive cells and B is a graph showing the number of TUNEL-positive cells per unit area.

FIG. 7 shows the effects of administration of *Triticum aestivum* Lamarck leaf extracts and fractions thereof on liver tissue of mice with liver injury induced by alcohol intake in accordance with an embodiment of the present invention.

FIG. 8 shows the effects of *Triticum aestivum* Lamarck leaf extracts and fractions thereof on GOT and GPT levels in serum of mice with liver injury induced by alcohol intake in accordance with an embodiment of the present invention, where A is a graph showing the results of GOT and B is a graph showing the results of GPT.

FIG. 9 is a graph showing the effects of administration of *Triticum aestivum* Lamarck leaf extracts and fractions thereof on GSH level in liver tissue of mice with liver injury induced by alcohol intake in accordance with an embodiment of the present invention.

FIG. 10 is a graph showing the effects of administration of *Triticum aestivum* Lamarck leaf extracts and fractions thereof on SOD level in liver tissue of mice with liver injury induced by alcohol intake in accordance with an embodiment of the present invention.

FIG. 11 shows the effects of *Triticum aestivum* Lamarck leaf extracts and fractions thereof on the inhibition of apoptosis of hepatocytes in mice with liver injury induced by alcohol intake in accordance with an embodiment of the present invention, where A shows images of TUNEL-positive cells and B is a graph showing the number of TUNEL-positive cells per unit area.

FIG. 12 shows the effects of administration of *Triticum aestivum* Lamarck leaf extracts and fractions thereof on liver tissue of mice with liver injury induced by acetaminophen in accordance with an embodiment of the present invention.

FIG. 13 shows the effects of *Triticum aestivum* Lamarck leaf extracts and fractions thereof on GOT and GPT levels in serum of mice with liver injury induced by acetaminophen in accordance with an embodiment of the present invention, where A is a graph showing the results of GOT and B is a graph showing the results of GPT.

FIG. 14 is a graph showing the effects of administration of *Triticum aestivum* Lamarck leaf extracts and fractions thereof on GSH level in liver tissue of mice with liver injury induced by acetaminophen in accordance with an embodiment of the present invention.

FIG. 15 is a graph showing the effects of administration of *Triticum aestivum* Lamarck leaf extracts and fractions thereof on SOD level in liver tissue of mice with liver injury induced by acetaminophen in accordance with an embodiment of the present invention.

FIG. 16 shows the effects of *Triticum aestivum* Lamarck leaf extracts and fractions thereof on the inhibition of apoptosis of hepatocytes in mice with liver injury induced by acetaminophen in accordance with an embodiment of the present invention, where A shows images of TUNEL-positive cells and B is a graph showing the number of TUNEL-positive cells per unit area.

DETAILED DESCRIPTION OF THE INVENTION

Hereinafter, the present invention will be described in detail.

In the following description, the term "*Triticum aestivum* Lamarck leaf" is meant to include young leaves or buds (wheat sprouts or buds), which sprout and grow from *Triticum aestivum* Lamarck seeds, and mature leaves.

The inventors of the present invention have conducted research using *Triticum aestivum* Lamarck leaves to develop new drugs for the prevention, improvement and treatment of liver injury and dysfunction and, as a result, confirmed the *Triticum aestivum* Lamarck leaf extracts and fractions thereof inhibit cytotoxicity caused by tertiary butyl hydroperoxide in HepG2 cell line cells, exhibiting cell protection activity, treat degeneration of liver tissue in mouse models with liver injury induced by LPS, alcohol, and acetaminophen, increase the synthesis of antioxidant enzymes such as GSH and SOD in liver tissue, and inhibit apoptosis of hepatocytes induced by liver injury, thereby recovering the liver function.

Therefore, the present invention provides a method for preventing, alleviating or treating a liver disease, comprising administering a composition comprising a *Triticum aestivum* Lamarck leaf extract or a fraction thereof to a subject in need thereof.

Moreover, the present invention provides a method for preventing or alleviating liver injury or dysfunction, comprising administering a composition comprising a *Triticum aestivum* Lamarck leaf extract or a fraction thereof to a subject in need thereof.

As used herein, the term "extract" refers to a preparation obtained by extraction of crude drugs, followed by evaporation and concentration, and may be a liquid extract obtained by extraction, a diluent or concentrate of the extract, or a crude purified product or purified product thereof. As used herein, the term "fraction" refers to a product obtained by fractionation to isolate a specific component or specific group from a mixture comprising various components. In the present invention, the fraction refers to a product obtained by fractionation to isolate a specific component or specific group from the *Triticum aestivum* Lamarck leaf extract.

The *Triticum aestivum* Lamarck leaf extract or the fraction thereof may be obtained by extraction, isolation, and fractionation of natural products using extraction, isolation, and fractionation methods known in the art. As defined herein, the "extract" is extracted from *Triticum aestivum* Lamarck leaves using a suitable solvent and may include a crude extract of *Triticum aestivum* Lamarck leaves, a polar solvent soluble extract, and a non-polar solvent soluble extract.

Examples of the suitable solvent used for the extraction of *Triticum aestivum* Lamarck leaf extracts may include, but not limited to, any pharmaceutically acceptable solvent such as water or an organic solvent. For example, the solvent may include one or more of purified water, alcohols having 1 to 4 carbon atoms, such as methanol, ethanol, propanol, isopropanol, and butanol, and mixtures thereof. Preferably, the use of a 15 to 50% (v/v) ethanol solvent can treat degeneration of liver tissue caused by liver injury, inhibit apoptosis of hepatocytes, and increase the synthesis of antioxidant enzymes such as glutathione (GSH) and superoxide dismutase (SOD) which can reduce oxidative stress in liver tissue.

The extraction may be performed at a temperature of 100° C. or lower, preferably 45° C. to 50° C. The extraction method may include room temperature extraction, hot water extraction, maceration extraction, reflux extraction, solvent extraction, water vapor distillation, ultrasonic extraction, elution, and compression, and in particular, it is more preferable to use the room temperature extraction.

Examples of the suitable solvent used to obtain the *Triticum aestivum* Lamarck leaf fraction may include, chloroform, ethyl acetate, butanol, or mixtures thereof, and it is preferable to obtain the fraction by sequential fractionation with chloroform, ethyl acetate and water. Preferably, among the fractions of *Triticum aestivum* Lamarck leaves obtained in the above-described manner, the use of a butanol fraction, a water fraction, or a mixture fraction thereof can treat degeneration of liver tissue caused by liver injury, inhibit apoptosis of hepatocytes, and increase the synthesis of antioxidant enzymes such as glutathione (GSH) and superoxide dismutase (SOD) which can reduce oxidative stress in liver tissue.

After obtaining the extract or the fraction thereof using water or an organic solvent as described above, it is possible to obtain a liquid phase product by macerating, heating and filtering the extract or the fraction thereof at room temperature by a method known in the art, and the solvent may be further evaporated, spray-dried or freeze-dried.

Moreover, the *Triticum aestivum* Lamarck leaf extract or the fraction thereof contained as an active ingredient in the composition of the present invention may be prepared in the form of powder by an additional process such as distillation under reduced pressure, freeze drying, or spray drying. Furthermore, it is possible to obtain a further purified fraction from the extract or the fraction thereof by various chromatography techniques, such as silica gel column chromatography, thin layer chromatography, high performance liquid chromatography, etc.

Therefore, the *Triticum aestivum* Lamarck leaf extract or the fraction thereof used in the present invention is a concept that encompasses all of the extracts, fractions, and purified products, which are obtained in each of the extraction, fractionation, and purification steps, and diluents, concentrates, and dried products thereof.

According to an embodiment of the present invention, the *Triticum aestivum* Lamarck leaf extract or the fraction thereof has excellent effects of inhibiting cytotoxicity caused by tertiary butyl hydroperoxide in HepG2 cell line cells to exhibit cell protection activity, treating degeneration of liver tissue in mouse models with liver injury induced by LPS, alcohol, and acetaminophen, increasing the synthesis of antioxidant enzymes such as GSH and SOD in liver tissue, and inhibiting apoptosis of hepatocytes induced by liver injury. Therefore, the present invention provides a method for preventing or treating liver injury or dysfunction and a liver disease caused thereby using the composition comprising the *Triticum aestivum* Lamarck leaf extract or the fraction thereof, and the composition can be effectively used as a pharmaceutical composition or a food composition.

Moreover, the composition comprising the *Triticum aestivum* Lamarck leaf extract or the fraction thereof of the present invention can be used as a food additive or a dietary supplement.

When the composition is used as a food additive, it can be properly used by adding the *Triticum aestivum* Lamarck leaf extract or the fraction thereof as it is or mixing the *Triticum aestivum* Lamarck leaf extract or the fraction thereof with other foods or food ingredients.

The liver diseases may include drug-induced liver disease, alcoholic liver disease, nonalcoholic liver disease, metabolic liver disease, infectious liver disease, etc. Specifically, the diseases caused by liver injury or dysfunction may include acute hepatitis, chronic hepatitis, steatosis, cirrhosis, liver fibrosis, liver cancer, drug-induced hepatitis, jaundice, etc.

The amount of the mixture of the *Triticum aestivum* Lamarck leaf extract and the fraction thereof may be suitably changed depending on the intended use (e.g., for prevention, health or therapeutic treatment), and the *Triticum aestivum* Lamarck leaf extract or the fraction thereof may preferably be contained in an amount of 0.01 to 95 wt % with respect to the total weight of the composition, more preferably 1 to 80 wt %. If the content is less than 0.01 wt %, the effect of the composition may be lowered, whereas, if it exceeds 95 wt %, it may be difficult to formulate the dosage form or it may be uneconomical because the rate of increase in effectiveness with respect to the amount of the extract or the fraction thereof used is low.

Specifically, for the production of food or beverage, the *Triticum aestivum* Lamarck leaf extract or the fraction thereof of the present invention may be added in an amount of 15 wt % or lower, preferably 10 wt % or lower with respect to the total weigh of the raw material. In the case of long-term intake for the purpose of health and hygiene or health control, it may be added in an amount less than the above range, and the active ingredient can be used in an amount greater than the above range because there is no problem in terms of safety.

Meanwhile, the composition of the present invention may be formulated into various dosage forms by conventional methods. For example, the composition of the present invention may be formulated into oral dosage forms such as powders, granules, tablets, capsules, suspensions, emulsions, syrups, etc., or in the form of external preparations, suppositories, and sterile injectable solutions. However, the composition of the present invention may preferably be provided in the form of a skin preparation for external use. Specifically, the composition of the present invention can be used in the form of skin preparations for external use such as liquids, ointments, creams, lotions, sprays, patches, gels, aerosols, etc.

Moreover, the composition of the present invention may further contain pharmaceutically acceptable carriers, excipients and diluents depending on the dosage form. Furthermore, the composition of the present invention may be formulated into preparations for external use, such as powders, granules, tablets, capsules, suspensions, emulsions, syrups, aerosols, etc., and in the form of sterile injectable solutions, and may preferably be used in the form of creams, gels, patches, sprays, ointments, oral preparations, lotions, liniments, pastes, or cataplasmas. For example, in the case of a skin preparation for external use that is used locally at the site, it may contain typical additives, such as preservatives, solvents that assist penetration of medicines, ointments, and softeners for creams, and may additionally contain typical carriers such as ethanol or oleyl alcohol. Suitable formulations known in the art can be found in Remington's Pharmaceutical Science, Mack Publishing Company, Easton Pa., but it is not limited thereto.

Examples of the carriers, excipients and diluents include lactose, dextrose, sucrose, oligosaccharide, sorbitol, mannitol, xylitol, erythritol, maltitol, starch, acacia gum, alginate, gelatin, calcium phosphate, calcium silicate, cellulose, methylcellulose, amorphous cellulose, polyvinyl pyrrolidone, water, methyl hydroxybenzoate, propyl hydroxybenzoate, talc, magnesium stearate, mineral oil, etc. The composition may be formulated into dosage forms by mixing with generally used diluents or excipients such as fillers, extenders, binders, wetting agents, disintegrating agents, surfactants, or excipients. Solid dosage forms for oral administration include tablets, pills, powders, granules capsules, etc., and these solid dosage forms may be prepared by mixing with one or more suitable excipients such as starch, calcium carbonate, sucrose, lactose, gelatin, etc. In addition to simple excipients, lubricants such as magnesium stearate, talc, etc, can be used. Liquid dosage forms for oral administration include suspensions, solutions for internal use, emulsions, syrups, etc. and may contain various excipients such as wetting agents, sweeteners, aromatics, preservatives, etc. in addition to generally used simple diluents such as water and liquid paraffin. Dosage forms for parenteral administration include sterilized aqueous solutions, non-aqueous solvents, suspensions, emulsions, freeze drying agents, suppositories, etc. Examples of non-aqueous solvents and suspensions may include propylene glycol, polyethyleneglycol, vegetable oils such as olive oil, injectable esters such as ethyl oleate, etc. Bases for suppositories may include witepsol, macrogol, Tween 61, cacao butter, Laurin, glycerogelatine, etc. These components may be added alone or in combination to the active ingredient, i.e., the *Triticum aestivum* Lamarck leaf extract or the fraction thereof.

As used herein, the term "administration" refers to the act of giving a pharmaceutical composition of the present invention to a subject by any suitable method.

The composition of the present invention may be administered in a therapeutically effective amount of an active ingredient or a pharmaceutical composition, which elicits the biological or medicinal response in a tissue system, animal or human that is being sought by a researcher, veterinarian, medical doctor or other clinician, which induces alleviation of the symptoms of the disease or disorder being treated. It will be apparent to those skilled in the art that the therapeutically effective amount of the composition of the present invention and the number of administrations may vary depending on desired effect. Therefore, the optimal dose to be administered can easily be determined by those skilled in the art and may be adjusted depending on the type of disease, the severity of disease, the content of the active ingredient and other ingredients contained in the composition, the type of dosage form, a patient's age, body weight, general health, gender, and diet, the time of administration, the route of administration, the secretion rate of the composition, the duration of treatment, and various other factors including other drugs used at the same time. The compositions of the present invention may be administered to a subject through a variety of routes including intravenous, intraperitoneal, intramuscular, intraarterial, oral, intracardiac, intramedullary, intradural, transdermal, intrarectal, subcutaneous, sublingual, or topical administration, but not limited thereto.

The composition of the present invention may be administered in an amount of 1 to 10,000 mg/kg/day and may be administered once a day or several times a day.

The composition of the present invention may be used for the prevention or treatment of liver diseases alone or in combination with surgery, radiation therapy, hormone therapy, chemotherapy, or methods using a biological response modifier.

Examples of the composition to which the *Triticum aestivum* Lamarck leaf extract or the fraction thereof of the present invention may be added include meat, sausages, bread, chocolates, candies, snacks, cookies, pizza, ramen, noodles, gums, dairy products including ice creams, various soups, beverages, teas, health drinks, alcoholic beverages, vitamin complexes, etc., and may include all traditional health foods.

When the composition of the present invention is prepared as a beverage, it may additionally contain various sweeteners or natural carbohydrates, like general beverages. Examples of the natural carbohydrates may include monosaccharides such as glucose, fructose, etc.; disaccharides such as maltose, sucrose, etc.; and polysaccharides, such as dextrin and cyclodextrin. Examples of the sweeteners may include natural sweeteners or synthetic sweetening agents such as saccharin, aspartame, etc. The natural carbohydrates may preferably be contained in an amount of about 0.01-10 wt % with respect to the total weight of the composition of the present invention, more preferably 0.01 to 0.1 wt %.

The composition of the present invention may contain various nutrients, vitamins, electrolytes, flavors, coloring agents, pectic acid and salts thereof, alginic acid and salts thereof, organic acids, protective colloidal thickeners, pH adjusters, stabilizers, preservatives, glycerin, alcohol, carbonating agents for use in carbonated beverages, etc., and may further contain fruit flesh for preparing natural fruit juice, fruit juice beverages and vegetable beverages, but not limited thereto. Such ingredients may be used alone or in combination. Although the amount of such additives is not significantly limited, it is preferable that the additives be contained in the range of 0.01-0.1 wt % with respect to the total weight of the composition of the present invention.

In the case of long-term intake for the purpose of health and hygiene or health control, the composition of the present invention used in the form of food can be administered for a long time because there is no problem in terms of safety.

Next, the present invention will be described in more detail with reference to the following examples, but these examples are merely for illustrative purposes and are not intended to limit the scope of the present invention.

EXAMPLE 1

Preparation of *Triticum aestivum* Lamarck Leaf Extracts

*Triticum aestivum* Lamarck was supplied from the National Institute of Food Science and sprouted and grown on sterile peat moss for germination in organic farming at a constant temperature (average $20\pm2°$ C.). For 2 to 3 weeks after germination, *Triticum aestivum* Lamarck leaves were harvested, freeze-dried, and then pulverized to a predetermined size to give a powder. Each 50 g of the powdered *Triticum aestivum* Lamarck freeze-dried sample was heated with shaking at 50° C. for 2 hours in each 500 ml of purified water and 15, 30, 50, and 70% (v/v) ethanol, respectively, to give extracts. Then, the resulting extracts were filtered, concentrated under vacuum with a rotary evaporator (N-1000, EYELA, Tokyo, Japan), and freeze-dried to give 5.64 g of water extract of *Triticum aestivum* Lamarck leaves and 8.75 g, 10.54 g, 16.23 g and 16.85 g of ethanol extracts of *Triticum aestivum* Lamarck leaves with different concentrations of ethanol (15, 30, 50 and 70%).

EXAMPLE 2

Preparation of *Triticum aestivum* Lamarck Leaf Fractions 10 g of the 30% ethanol extract prepared in Example 1 was dissolved in 100 ml of distilled water, and then the chloroform ($CHCl_3$) layer was isolated and concentrated under reduced pressure to give 0.63 g of the chloroform fraction of *Triticum aestivum* Lamarck leaves. Ethyl acetate ($CH_3COOC_2H_5$) and butanol (n-butanol, $C_4H_9OH$) were sequentially added to the remaining water layer and then fractionated in the same manner as the chloroform layer to give 1.25 g of the ethyl acetate fraction of *Triticum aestivum* Lamarck leaves and 3.12 g of the butanol fraction of *Triticum aestivum* Lamarck leaves, and 4.57 g of the water fraction of *Triticum aestivum* Lamarck leaves.

EXAMPLE 3

Analysis of the Effects of *Triticum aestivum* Lamarck Leaf Extracts and Fractions Thereof on the Improvement of Hepatocyte Injury in HepG2 Cell Lines 3-1. Culture of HepG2 Cells HepG2 cells, a liver cancer cell line, were cultured in DMEM (Thermo Scientific Hyclone) containing 10% fetal bovine serum, 1% penicillin (100 units/ml), and streptomycin (100 µg/ml) in an incubator at 37° C. and 5% $CO_2$.

3-2. Effects of *Triticum aestivum* Lamarck Leaf Extracts and Fractions Thereof on the Improvement of Hepatocyte Injury Induced by Tertiary Butyl Hydroperoxide In order to analyze the effects of the *Triticum aestivum* Lamarck leaf extracts and fractions thereof on the protection of hepatocytes, the effects of tertiary butyl hydroperoxide, which causes oxidative stress, on cell damage were analyzed. HepG2 cells cultured in Example 3-1 was seeded in a 48-well plate at $5\times10_4$ cells/well and maintained for 24 hours. Then, the *Triticum aestivum* Lamarck leaf extracts (the water extract, and the 15, 30, 50, and 70% ethanol extracts (100 g/ml)) and the fractions thereof (the chloroform, ethyl acetate, butanol, and water fractions (4, 20, 100 µg/ml) fractionated from the 30% ethanol extract) were pre-treated in media and then cultured for 24 hours. After 24 hours of culture, the cells were washed with phosphate buffered saline, treated with 1 mM of tert-butyl hydroperoxide (t-BHP), and cultured for 3 hours to induce apoptosis of hepatocytes. Media were changed after 3 hours, 20 µl of CCK-8 reagent was added, and the cells were further cultured for 1 hour. The absorbance at 450 nm was measured from the culture media of cultured cells using a microplate reader, and the results are shown in FIG. 1.

As shown in FIG. 1, the cell viability was decreased due to hepatocyte injury in the group treated with tertiary butyl hydroperoxide, compared to the untreated group (ctl). It was found that HepG2 hepatocyte injury induced by tertiary butyl hydroperoxide was significantly improved in the group treated with the 15%, 30%, and 50% ethanol extracts, among the experimental groups treated with the water extract of *Triticum aestivum* Lamarck leaves and the ethanol extracts with different concentrations (FIG. 1A). As a result of treatment with the fractions fractionated from the 30% ethanol extract which showed the most significant improvement effect, it was found that HepG2 hepatocyte injury induced by tertiary butyl hydroperoxide was significantly improved in the group treated with the butanol and water fractions of *Triticum aestivum* Lamarck leaves at concentrations of 20 and 100 µg/ml, resulting in promotion of cell proliferation.

According to these experimental results, the effects of the 30% ethanol extract of *Triticum aestivum* Lamarck leaves, the butanol fraction of *Triticum aestivum* Lamarck leaves, and the water fraction of *Triticum aestivum* Lamarck leaves on the improvement of liver tissue injury in animal models were observed.

EXAMPLE 4

Effects of *Triticum aestivum* Lamarck Leaf Extracts and Fractions Thereof on Mice with Liver Injury Induced by LPS 4-1. Construction of LPS-Induced Liver Injury Models Experimental animals, 6 to 8 week-old C57BL/6 male mice weighing 22 to 25 g, were purchased from Samtako (Osan, Korea). The experimental animals were fed with standard diet and water and allowed to acclimate to animal laboratory conditions at a temperature of $22\pm2°$ C. and a humidity of $50\pm5\%$ for 1 week. After 1 week, the experimental animals were divided into a total of 6 groups with 5 mice per group, including a normal group (Normal), a positive control group (LPS), a group treated with the 30% ethanol extract of *Triticum aestivum* Lamarck leaves (TA EtOH Ex. 100 mg/kg/day), a group treated with the butanol fraction of *Triticum aestivum* Lamarck leaves (TA BuOH Fr. 100 mg/kg/day), a group treated with the water fraction of *Triticum aestivum* Lamarck leaves (TA $H_2O$ Fr. 100 mg/kg/day), an experimental control group (Silymarin, 100 mg/kg/day). The experimental animals were orally administered with the *Triticum aestivum* Lamarck leaf extracts or the fractions thereof once a day for 2 days and then injected intraperitoneally with 1 mg/kg of LPS to induce liver injury. After 12 hours, the mice were sacrificed, and their blood and liver tissues were collected. These experiments were conducted in accordance with ethical regulations with the approval of the Chonbuk National University Institutional Animal Care and Use Committee.

4-2. Morphological Analysis of Mice with Liver Injury Induced by LPS

A certain portion of the left lobe of the liver tissue was collected from each of the experimental animals with liver injury induced by LPS in Example 4-1 and immediately fixed in 10% neural formalin. The fixed tissue was frozen in OCT compound and then sliced with a microtome into tissue sections having a thickness of 10 μm. The tissue sections were stained with hematoxylin and eosin, and then the morphological changes were observed under optical microscope. The results are shown in FIG. 2.

As shown in FIG. 2, it was found that excessive formation of vacuoles and loss of nucleus occurring in liver tissue resulted in degeneration of liver tissue in the positive control group with liver injury induced by LPS compared to the normal group, while the formation of vacuoles was decreased and the structural degeneration was inhibited in the experimental groups administered with the ethanol extract of *Triticum aestivum* Lamarck leaves and the butanol and water fractions of *Triticum aestivum* Lamarck leaves of the present invention.

4-3. Effects of *Triticum aestivum* Lamarck Leaf Extracts and Fractions Thereof on the Levels of GOT and GPT in Serum of Mice with Liver Injury Induced by LPS The blood collected from the experimental animals with liver injury induced by LPS in Example 4-1 was centrifuged to separate the serum, and the levels of GOT and GPT enzymes, which are indicators of liver injury, were measured. The levels of GOT and GPT in serum were measured with ALT/AST(GPT/GOT) cassette test provided by Alere, and the results are shown in FIG. 3.

As shown in FIG. 3, it was found that the level of GOT in serum was significantly increased in the positive control group with liver injury induced by LPS compared to the normal group, whereas the level of GOT in serum was significantly reduced in the experimental groups administered with the ethanol extract of *Triticum aestivum* Lamarck leaves and the butanol and water fractions of *Triticum aestivum* Lamarck leaves of the present invention (FIG. 3A). It was also found that the level of GPT in serum was increased in the positive control group with liver injury induced by LPS compared to the normal group, whereas the level of GPT in serum was significantly reduced in the experimental groups administered with the ethanol extract of *Triticum aestivum* Lamarck leaves and the butanol and water fractions of *Triticum aestivum* Lamarck leaves of the present invention (FIG. 3B).

4-4. Effects of *Triticum aestivum* Lamarck Leaf Extracts and Fractions Thereof on the Level of GSH in Liver Tissue of Mice with Liver Injury Induced by LPS The liver tissues extracted from the experimental animals sacrificed in Example 4-1 were washed with cold saline, weighed, and then homogenized in saline containing 5% meta-phosphoric acid. Homogenized liver tissues were centrifuged at 14,000×g at 4° C. for 15 minutes, and then the supernatants were collected. The level of GSH in liver tissue was measured from the collected supernatants using a glutathione (total) detection kit provided by Enzo life science, and the results are shown in FIG. 4.

As shown in FIG. 4, it was found that the level of GSH in liver tissue was decreased in the positive control group with liver injury induced by LPS compared to the normal group, whereas the level of GSH in liver tissue was significantly increased in the experimental groups administered with the ethanol extract of *Triticum aestivum* Lamarck leaves and the butanol and water fractions of *Triticum aestivum* Lamarck leaves of the present invention.

4-5. Effects of *Triticum aestivum* Lamarck Leaf Extracts and Fractions Thereof on the Level of SOD in Liver Tissue of Mice with Liver Injury Induced by LPS In order to measure the level of SOD in liver tissue of the experimental animals collected in Example 4-1, the liver tissues were washed with a phosphate buffer solution and homogenized, and then the cell pellets were collected. Cytoplasmic extracts from cell pellets were prepared according to the instructions of the SOD Assay Kit-WST provided by Dojindo. The absorbance at 450 nm was measured to analyze the SOD activity in liver tissue, and the results are shown in FIG. 5.

As shown in FIG. 5, it was found that the level of SOD in liver tissue was decreased in the positive control group with liver injury induced by LPS compared to the normal group, whereas the level of SOD in liver tissue was significantly increased in the experimental groups administered with the ethanol extract of *Triticum aestivum* Lamarck leaves and the butanol and water fractions of *Triticum aestivum* Lamarck leaves of the present invention.

4-6. Effects of *Triticum aestivum* Lamarck Leaf Extracts and Fractions Thereof on the Inhibition of Apoptosis of Hepatocytes in Mice with Liver Injury Induced by LPS In order to determine whether the *Triticum aestivum* Lamarck leaf ethanol extracts and the butanol and water fractions thereof of the present invention can inhibit apoptosis of hepatocytes due to livery injury induced by LPS in the experimental animals, the liver tissues collected in Example 4-1 were fixed in 10% formalin, and 10 μm frozen sections were prepared. Then, terminal deoxynucleotidyl transferase-mediated dUTP nick end labeling (TUNEL) assay was performed using a TUNEL apoptosis detection kit from Millipore according to the instructions of the manufacturer. Each tissue section was observed under fluorescence microscope, and the results are shown in FIG. 6.

As shown in FIG. 6, it was found that the number of TUNEL-positive cells in liver tissue was significantly increased by administration of LPS in the positive control group, whereas the number of TUNEL-positive cells in liver tissue was significantly reduced in the experimental groups administered with the ethanol extract of *Triticum aestivum* Lamarck leaves and the butanol and water fractions of *Triticum aestivum* Lamarck leaves of the present invention (FIG. 6A). It was also found from the cell numbers observed under high-magnification microscope that the number of TUNEL-positive cells in liver tissue was significantly reduced in the experimental groups administered with the ethanol extract of *Triticum aestivum* Lamarck leaves and the butanol and water fractions of *Triticum aestivum* Lamarck leaves of the present invention, resulting in inhibition of apoptosis of hepatocytes (FIG. 6B).

EXAMPLE 5

Effects of *Triticum aestivum* Lamarck Leaf Extracts and Fractions Thereof on Mice with Liver Injury Induced by Alcohol Intake 5-1. Construction of Alcohol Intake-Induced Liver Injury Models Experimental animals, 6 to 8 week-old C57BL/6 male mice weighing 22 to 25 g were purchased from Samtako (Osan, Korea). The experimental animals were fed with standard diet and water and allowed to acclimate to vivarium conditions (animal laboratory conditions) at a temperature of 22±2° C. and a humidity of 50±5% for 1 week. After acclimation, the experimental animals were divided into a total of 6 groups with 5 mice per group, including a normal group (Normal), a positive control group (Et-OH), a group treated with the 30% ethanol extract of *Triticum aestivum* Lamarck leaves (TA EtOH Ex. 100 mg/kg/day), a group treated with the butanol fraction of *Triticum aestivum* Lamarck leaves (TA BuOH Fr. 100 mg/kg/day), a group treated with the water fraction of *Triticum aestivum* Lamarck leaves (TA H$_2$O Fr. 100 mg/kg/day), an experimental control group (Silymarin, 100 mg/kg/day). Except for the normal group, a 5% ethanol solution was orally administered to the experimental groups once a day for 10 days and a 20% ethanol solution was given on the 11$^{th}$ day of the experiment. The *Triticum aestivum* Lamarck leaf extracts or the fractions thereof were orally administered at a fixed time once a day for 11 days over the whole period of the experiment. After the experiment, the animals were sacrificed under anesthesia, and their blood and liver tissues were collected. These experiments were conducted in accordance with ethical regulations with the approval of the Chonbuk National University Institutional Animal Care and Use Committee.

5-2. Morphological Analysis of Mice with Liver Injury Induced by Alcohol Intake

A certain portion of the left lobe of the liver tissue was collected from each of the experimental animals with liver injury induced by alcohol intake in Example 5-1. The morphological changes in liver tissue were observed under optical microscope in the same manner as Example 4-2, and the results are shown in FIG. 7.

As shown in FIG. 7, it was found that excessive formation of vacuoles and loss of nucleus occurring in liver tissue resulted in degeneration of liver tissue in the positive control group with liver injury induced by alcohol intake compared to the normal group, while the structural degeneration was inhibited in the experimental groups administered with the ethanol extract of *Triticum aestivum* Lamarck leaves and the butanol and water fractions of *Triticum aestivum* Lamarck leaves of the present invention.

5-3. Effects of *Triticum aestivum* Lamarck Leaf Extracts and Fractions Thereof on the Levels of GOT and GPT in Serum of Mice with Liver Injury Induced by Alcohol Intake Blood was collected from the experimental animals with liver injury induced by alcohol intake in Example 5-1, and the levels of GOT and GPT in serum were analyzed in the same manner as in Example 4-3. The results are shown in FIG. 8.

As shown in FIG. 10, it was found that the level of GOT in serum was significantly increased in the positive control group with liver injury induced by alcohol intake compared to the normal group, whereas the level of GOT in serum was reduced in the experimental groups administered with the ethanol extract of *Triticum aestivum* Lamarck leaves and the butanol and water fractions of *Triticum aestivum* Lamarck leaves of the present invention (FIG. 8A). It was also found that the level of GPT in serum was increased in the positive control group with liver injury induced by alcohol intake compared to the normal group, whereas the level of GPT in serum was significantly reduced in the experimental groups administered with the ethanol extract of *Triticum aestivum* Lamarck leaves and the butanol and water fractions of *Triticum aestivum* Lamarck leaves of the present invention (FIG. 8B).

5-4. Effects of *Triticum aestivum* Lamarck Leaf Extracts and Fractions Thereof on the Level of GSH in Liver Tissue of Mice with Liver Injury Induced by Alcohol Intake The level of GSH in liver tissue was measured from the liver tissues collected in Example 5-1 in the same manner as in Example 4-4, and the results are shown in FIG. 9.

As shown in FIG. 9, it was found that the level of GSH in liver tissue was decreased in the positive control group with liver injury induced by alcohol intake compared to the normal group, whereas the level of GSH in liver tissue was significantly increased in the experimental groups administered with the ethanol extract of *Triticum aestivum* Lamarck leaves and the butanol and water fractions of *Triticum aestivum* Lamarck leaves of the present invention.

5-5. Effects of *Triticum aestivum* Lamarck Leaf Extracts and Fractions Thereof on the Level of SOD in Liver Tissue of Mice with Liver Injury Induced by Alcohol Intake The level of SOD in liver tissue of the experimental animals collected in Example 5-1 was analyzed in the same manner as in Example 4-5, and the results are shown in FIG. 10.

As shown in FIG. 10, it was found that the level of SOD in liver tissue was decreased in the positive control group with liver injury induced by alcohol intake compared to the normal group, whereas the level of SOD in liver tissue was significantly increased in the experimental groups administered with the ethanol extract of *Triticum aestivum* Lamarck leaves and the butanol and water fractions of *Triticum aestivum* Lamarck leaves of the present invention.

5-6. Effects of *Triticum aestivum* Lamarck Leaf Extracts and Fractions Thereof on the Inhibition of Apoptosis of Hepatocytes in Mice with Liver Injury Induced by Alcohol Intake In order to determine whether the *Triticum aestivum* Lamarck leaf ethanol extracts and the butanol and water fractions thereof of the present invention can inhibit apoptosis of hepatocytes due to livery injury induced by alcohol intake in the experimental animals, the liver tissues collected from the experimental animals in Example 5-1 were observed and analyzed in the same manner as Example 4-6, and the results are shown in FIG. 11.

As shown in FIG. 11, it was found that the number of TUNEL-positive cells in liver tissue was significantly increased by alcohol intake in the positive control group, whereas the number of TUNEL-positive cells in liver tissue was significantly reduced in the experimental groups administered with the ethanol extract of *Triticum aestivum* Lamarck leaves and the butanol and water fractions of *Triticum aestivum* Lamarck leaves of the present invention (FIG. 11A). It was also found from the cell numbers observed under high-magnification microscope that the number of TUNEL-positive cells in liver tissue was significantly reduced in the experimental groups administered with the ethanol extract of *Triticum aestivum* Lamarck leaves and the butanol and water fractions of *Triticum aestivum* Lamarck leaves of the present invention, resulting in inhibition of apoptosis of hepatocytes (FIG. 11B).

EXAMPLE 6

Effects of *Triticum aestivum* Lamarck Leaf Extracts and Fractions Thereof on Mice with Liver Injury Induced by Acetaminophen 6-1. Construction of Acetaminophen-Induced Liver Injury Models Experimental animals, 6 to 8 week-old C57BL/6 male mice were purchased from Samtako (Osan, Korea). The experimental animals were fed with standard diet and water and allowed to acclimate to animal laboratory conditions at a temperature of 22±2° C. and a humidity of 50±5% for 1 week. After acclimation, the experimental animals were divided into a total of 6 groups with 5 mice per group, including a normal group (Normal), a positive control group (acetaminophen, APAP), a group treated with the 30% ethanol extract of *Triticum aestivum* Lamarck leaves (TA EtOH Ex. 100 mg/kg/day), a group treated with the butanol fraction of *Triticum aestivum* Lamarck leaves (TA BuOH Fr. 100 mg/kg/day), a group treated with the water fraction of *Triticum aestivum* Lamarck leaves (TA H$_2$O Fr. 100 mg/kg/day), an experimental control group (Silymarin, 100 mg/kg/day). The *Triticum aestivum* Lamarck leaf extracts or the fractions thereof were orally administered to the experimental animals once a day for 7 days and then injected intraperitoneally with 300 mg/kg of acetaminophen to induce liver injury. These experiments were conducted in accordance with ethical regulations with the approval of the Chonbuk National University Institutional Animal Care and Use Committee.

6-2. Morphological Analysis of Mice with Liver Injury Induced by Acetaminophen

A certain portion of the left lobe of the liver tissue was collected from each of the experimental animals with liver injury induced by acetaminophen in Example 6-1. The morphological changes in liver tissue were observed under optical microscope in the same manner as Example 4-2, and the results are shown in FIG. 12.

As shown in FIG. 12, it was found that excessive formation of vacuoles and loss of nucleus occurring in liver tissue resulted in degeneration of liver tissue in the positive control group with liver injury induced by acetaminophen compared to the normal group, while the structural degeneration was inhibited in the experimental groups administered with the ethanol extract of *Triticum aestivum* Lamarck leaves and the butanol and water fractions of *Triticum aestivum* Lamarck leaves of the present invention.

6-3. Effects of *Triticum aestivum* Lamarck Leaf Extracts and Fractions Thereof on the Levels of GOT and GPT in Serum of Mice with Liver Injury Induced by Acetaminophen Blood was collected from the experimental animals with liver injury induced by acetaminophen in Example 6-1, followed by centrifugation to separate the serum, and the levels of GOT and GPT in serum were analyzed in the same manner as in Example 4-3. The results are shown in FIG. 13.

As shown in FIG. 13, it was found that the level of GOT in serum was significantly increased in the positive control group with liver injury induced by acetaminophen compared to the normal group, whereas the level of GOT in serum was reduced in the experimental groups administered with the ethanol extract of *Triticum aestivum* Lamarck leaves and the butanol and water fractions of *Triticum aestivum* Lamarck leaves of the present invention (FIG. 13A). It was also found that the level of GPT in serum was increased in the positive control group with liver injury induced by acetaminophen compared to the normal group, whereas the level of GPT in serum was significantly reduced in the experimental groups administered with the ethanol extract of *Triticum aestivum* Lamarck leaves and the butanol and water fractions of *Triticum aestivum* Lamarck leaves of the present invention (FIG. 13B).

6-4. Effects of *Triticum aestivum* Lamarck Leaf Extracts and Fractions Thereof on the Level of GSH in Liver Tissue of Mice with Liver Injury Induced by Acetaminophen The liver tissues extracted from the experimental animals in Example 6-1 were washed with cold saline and weighed. The level of GSH in liver tissue was measured in the same manner as Example 4-4, and the results are shown in FIG. 14.

As shown in FIG. 14, it was found that the level of GSH in liver tissue was decreased in the positive control group with liver injury induced by acetaminophen compared to the normal group, whereas the level of GSH in liver tissue was significantly increased in the experimental groups administered with the ethanol extract of *Triticum aestivum* Lamarck leaves and the butanol and water fractions of *Triticum aestivum* Lamarck leaves of the present invention.

6-5. Effects of *Triticum aestivum* Lamarck Leaf Extracts and Fractions Thereof on the Level of SOD in Liver Tissue of Mice with Liver Injury Induced by Acetaminophen The level of SOD in liver tissue of the experimental animals collected in Example 6-1 was analyzed in the same manner as in Example 4-5, and the results are shown in FIG. 15.

As shown in FIG. 15, it was found that the level of SOD in liver tissue was decreased in the positive control group with liver injury induced by acetaminophen compared to the normal group, whereas the level of SOD in liver tissue was significantly increased in the experimental groups administered with the ethanol extract of *Triticum aestivum* Lamarck leaves and the butanol and water fractions of *Triticum aestivum* Lamarck leaves of the present invention.

6-6. Effects of *Triticum aestivum* Lamarck Leaf Extracts and Fractions Thereof on the Inhibition of Apoptosis of Hepatocytes in Mice with Liver Injury Induced by Acetaminophen In order to determine whether the *Triticum aestivum* Lamarck leaf ethanol extracts and the fractions thereof of the present invention can inhibit apoptosis of hepatocytes due to livery injury induced by acetaminophen in the experimental animals, the liver tissues collected from the experimental animals in Example 6-1 were observed and analyzed in the same manner as Example 4-6, and the results are shown in FIG. 16.

As shown in FIG. 16, it was found that the number of TUNEL-positive cells in liver tissue was increased by administration of acetaminophen in the positive control group, whereas the number of TUNEL-positive cells in liver tissue was significantly reduced in the experimental groups administered with the ethanol extract of *Triticum aestivum* Lamarck leaves and the butanol and water fractions of *Triticum aestivum* Lamarck leaves of the present invention (FIG. 16A). It was also found from the cell numbers observed under high-magnification microscope that the number of TUNEL-positive cells in liver tissue was significantly reduced in the experimental groups administered with the ethanol extract of *Triticum aestivum* Lamarck leaves and the butanol and water fractions of *Triticum aestivum* Lamarck leaves of the present invention, resulting in inhibition of apoptosis of hepatocytes (FIG. 16B).

As described above, the present invention can provide a method useful for the prevention, improvement, or treatment of liver diseases, comprising administering a composition comprising a *Triticum aestivum* Lamarck leaf extract or a fraction thereof to a subject in need thereof, thereby alleviating the morphological change of liver tissue due to liver injury, inhibiting apoptosis of hepatocytes, increasing the synthesis of antioxidant enzymes such as glutathione (GSH) and superoxide dismutase (SOD) which can reduce oxidative stress in liver tissue, and reducing the levels of glutamic oxaloacetic transaminase (GOT) and glutamic pyruvic transaminase (GPT) which are known to change sensitively in liver diseases.

While the invention has been shown and described with reference to certain preferred embodiments thereof, it will be understood by those skilled in the art that various changes in form and details may be made therein without departing from the spirit and scope of the invention as defined by the appended claims. Therefore, the scope of the invention is defined not by the detailed description of the invention but by the appended claims, and all differences within the scope will be construed as being included in the present invention.

The invention claimed is:

1. A method for improving or treating a liver disease, comprising administering a composition containing an effective amount of a *Triticum aestivum* Lamarck leaf butanol fraction or water fraction thereof to a subject in need of the improvement or treatment, wherein the liver disease is acetaminophen-induced liver disease or alcoholic liver disease.

2. The method of claim 1, wherein the *Triticum aestivum* Lamarck leaf butanol fraction or water fraction thereof is contained in an amount of 0.01 to 95 wt % with respect to the total weight of the composition.

3. The method of claim 1, wherein the *Triticum aestivum* Lamarck leaf butanol fraction or water fraction thereof improves the morphological change of liver tissue due to liver injury and apoptosis.

4. The method of claim 1, wherein the *Triticum aestivum* Lamarck leaf butanol fraction or water fraction thereof increases the synthesis of an antioxidant enzyme, the antioxidant enzyme being capable of reducing oxidative stress in liver tissue.

5. A method for treating liver injury or improving or treating liver dysfunction, comprising administering a composition containing an effective amount of a *Triticum aestivum* Lamarck leaf butanol fraction or water fraction thereof to a subject in need of the treatment or improvement, wherein the liver injury or liver dysfunction is caused by alcohol or acetaminophen.

6. The method of claim 4, wherein the antioxidant enzyme is glutathione or superoxide dismutase.

* * * * *